United States Patent [19]
Schmitt et al.

[11] 3,991,766
[45] Nov. 16, 1976

[54] CONTROLLED RELEASE OF MEDICAMENTS USING POLYMERS FROM GLYCOLIC ACID

[75] Inventors: Edward Emil Schmitt, Palo Alto, Calif.; Rocco Albert Polistina, Port Chester, N.Y.

[73] Assignee: American Cyanamid Company, Stamford, Conn.

[22] Filed: Apr. 3, 1975

[21] Appl. No.: 564,969

Related U.S. Application Data

[63] Continuation-in-part of Ser. No. 365,656, May 31, 1973, Pat. No. 3,875,937, which is a continuation-in-part of Ser. No. 157,521, June 28, 1971, Pat. No. 3,739,773, which is a continuation-in-part of Ser. No. 852,617, Aug. 25, 1969, Pat. No. 3,620,218, which is a continuation-in-part of Ser. No. 608,086, Jan. 9, 1967, Pat. No. 3,463,158, which is a continuation-in-part of Ser. No. 320,543, Oct. 31, 1963, Pat. No. 3,297,033.

[52] U.S. Cl............................... 128/335.5; 424/19; 424/22; 424/28

[51] Int. Cl.².......................................... A61L 17/00
[58] Field of Search ........... 128/335.5, 335; 424/19, 424/22, 28

[56] References Cited
UNITED STATES PATENTS

| | | | |
|---|---|---|---|
| 3,297,033 | 1/1967 | Schmitt et al..................... | 128/335.5 |
| 3,773,919 | 11/1973 | Boswell et al........................ | 424/19 |
| 3,887,699 | 6/1975 | Yolles............................. | 128/260 X |

*Primary Examiner*—Dalton L. Truluck
*Attorney, Agent, or Firm*—Samuel Branch Walker

[57] ABSTRACT

Polyhydroxyacetic ester, also called polyglycolic acid (PGA), has surgically useful mechanical properties. On implantation, in living mammalian tissue, the polyglycolic acid is absorbed, and replaced by living tissue. Sutures, clips and storage pellets having medicaments incorporated therein can be used for both their own mechanical properties and as a delayed release system for medicaments.

5 Claims, No Drawings

CONTROLLED RELEASE OF MEDICAMENTS USING POLYMERS FROM GLYCOLIC ACID

CROSS REFERENCES

This application is a continuation-in-part of Ser. No. 365,656, filed May 31, 1973, now U.S.Pat. No. 3,875,937, dated Apr. 8, 1975, SURGICAL DRESSINGS OF ABSORBABLE POLYMERS, which is a continuation-in-part of Ser. No. 157,521, filed June 28, 1971, now U.S. Pat. No. 3,739,773, June 19, 1973, POLYGLYCOLIC ACID PROSTHETIC DEVICES, which is a continuation-in-part of Ser. No. 852,617, Aug. 25, 1969, now U.S. Pat. No. 3,620,218, Nov. 16, 1971, CYLINDRICAL PROSTHETIC DEVICES OF POLYGLYCOLIC ACID, which is a continuation-in-part of Ser. No. 608,086, Jan. 9, 1967, now U.S. Pat. No. 3,463,158, Aug. 26, 1969, POLYGLYCOLIC ACID PROSTHETIC DEVICES which is a continuation-in-part of Ser. No. 320,543, filed Oct. 31, 1963, now U.S. Pat. No. 3,297,033, Jan. 10, 1967, SURGICAL SUTURES. Reference is made to said earlier patents for certain prior art and definitions there set forth.

Related data incorporated herein by this reference on manufacturing of polyglycolic acid, producing surgical elements thereof and its use for surgical purposes, additional prior art and definitions, are disclosed in:

U.S. Pat. No. 3,414,939 — Dec. 10, 1968, Chirgwin, APPARATUS FOR QUENCHING MELT-SPUN FIBERS.

U.S. 3,422,181 — Jan. 14, 1969, Chirgwin, METHOD FOR HEAT SETTING OF STRETCH ORIENTED POLYGLYCOLIC ACID FILAMENT.

U.S. Pat. No. 3,435,008 — March 25, 1969, Schmitt, Epstein, and Polistina, METHOD FOR PREPARATION OF ISOMERICALLY PURE β-GLYCOLIDE AND POLYMERIZATION METHOD FOR GLYCOLIDE COMPOSITIONS AND POLYMERIZATION METHOD FOR GLYCOLIDE COMPOSITIONS EMPLOYING PARTIAL HYDROLYZATE OF SAID β-GLYCOLIDE.

U.S.Pat. No. 3,442,871 —May 6, 1969, Schmitt, Epstein and Polistina, PROCESS FOR POLYMERIZING A GLYCOLIDE.

U.S. 3,457,280 — July 22, 1969, Schmitt, Epstein and Polistina, α-GLYCOLIDE AND METHODS FOR THE ISOLATION THEREOF.

U.S. Pat. No. 3,468,853 — Sept. 23, 1969, Schmitt and Polistina, PROCESS OF POLYMERIZING A GLYCOLIDE.

U.S. Pat. No. 3,565,077 — Feb. 23, 1971, Glick, DENSIFIED ABSORBABLE POLYGLYCOLIC ACID SUTURE BRAID, AND METHOD FOR PREPARING SAME.

U.S. Pat. No. 3,565,869 — Feb. 23, 1971, DeProspero, EXTRUDABLE AND STRETCHABLE POLYGLYCOLIC ACID AND PROCESS FOR PREPARING SAME.

U.S. Pat. No. 3,597,449 — Aug. 3, 1971, DeProspero and Schmitt, STABLE GLYCOLIDE AND LACTIDE COMPOSITIONS.

U.S. Pat. No. 3,597,450 — Aug. 3, 1971, Schmitt, Polistina, Epstein and DeProspero, PREPARATION OF GLYCOLIDE POLYMERIZABLE INTO POLYGLYCOLIC ACID OF CONSISTENTLY HIGH MOLECULAR WEIGHT.

U.S. Pat. No. 3,600,223, — Aug. 17, 1971, Glick and McCusker, PROCESS FOR CLEANING POLYGLYCOLIC ACID FILAMENTS USEFUL AS ABSORBABLE SURGICAL SUTURES.

U.S. Pat. No. 3,626,948, — Dec. 14, 1971, Glick and McPherson, ABSORBABLE POLYGLYCOLIC ACID SUTURE OF ENHANCED IN-VIVO STRENGTH RETENTION.

U.S. Pat. No. 3,728,739 — Apr. 24, 1973, Semp, STERILE SURGICAL GLOVES.

U.S. Pat. No. 3,728,839 — Apr. 24, 1973, Glick, STORAGE STABLE SURGICALLY ABSORBABLE POLYGLYCOLIC ACID PRODUCTS.

U.S. Ser. No. 118,974, Feb. 25, 1971, Ramsey and Delapp, PREPARATION OF POLYGLYCOLIC ACID IN FINELY DIVIDED FORM, now U.S. Pat. No. 3,781,349, Dec. 25, 1973.

U.S. Ser. No. 171,320, Aug. 12, 1971, Schmitt and Bailey, POLYGLYCOLIC ACID IN SOLUTIONS, now U.S. Pat. 3,737,440, June 5, 1973.

U.S. Ser. No. 176,291, Aug. 30, 1971, Glick and Chirgwin, DOPE-DYED POLYGLYCOLIC ACID SUTURES.

U.S. Ser. No. 190,290, Oct. 18, 1971, Schmitt and Epstein, COPOLYMERS ABSORBABLE BY LIVING MAMMALIAN TISSUES, now U.S. Pat. No. 3,736,646, June 5, 1973, METHOD OF ATTACHING SURGICAL NEEDLES TO MULTIFILAMENT POLYGLYCOLIC ACID ABSORBABLE SUTURES. A continuation-in-part thereof, U.S. Ser. No. 354,043, filed Apr. 24, 1973, is now U.S. Pat. No. 3,867,190, Feb. 18, 1975, Schmitt and Epstein, REDUCING CAPILLARITY OF POLYCOLIC ACID SUTURES. This patent cites some art here pertinent.

U.S. Ser. No. 277,537, Aug. 3, 1972, Glick and Chirgwin, GREEN POLYGLYCOLIC ACID SUTURES AND SURGICAL ELEMENTS.

U.S. Pat. No. 2,552,027, Bird and Rochow, May 8, 1951, CASTING GELATIN TABLETS, in Column 6, line 18 and following shows gelatin formulations for slow and uniform release of therapeutic agents from a carrier matrix.

U.S. Pat. No. 3,773,919, Boswell and Scribner, POLYLACTIDE-DRUG MIXTURES, Nov. 20, 1973, discloses sustained release drugs using a lactide/glycolide copolymer as a carrier matrix. Such polymers are soluble in common organic solvents. This patent lists many drugs which may be incorporated in controlled release carriers. This list is hereby incorporated herein by this reference thereto.

Other United States and foreign patents disclose surgical elements in which biodegradability and absorption results from the hydrolytic attack of tissue components on glycolic acid ester linkages in the polymer composing such surgical elements.

FIELD OF INVENTION

This invention relates to absorbable surgical elements of polyglycolic acid (PGA), which have incorporated therein a drug or medicament which is released into tissue as the PGA is absorbed. A simple but effective implant is a surgical suture containing an antibiotic — the suture serves its usual purpose of retaining tissue in location. The antibiotic aids in controlling the propagation of pathogenic organisms if such are present in the wound being sutured. The antibiotic is released during the period during which pathogenic organisms are most likely to contaminate the wound. At the time of use, such elements should be sterile.

A "repository" is a composite of a medicament and a carrier whereby the medicament is placed in a desired location, and released slowly by the carrier so that the effective therapeutic action of the medicament is extended. Slowly digestible drug release devices, including pills and pellets, may be inserted subcutaneously, or orally, or into any body cavity where slowed release of the medicament is desired. Digestible carriers are preferred. The digestion may be in the intestinal tract or in tissue depending on the desired administrative site. An absorbable suture impregnated with a drug may be used to suture tissue and release the drug, or as primarily a source of the drug.

For different purposes and in different types of tissue the rate of absorption may vary. In general, an absorbable suture or solid load bearing prosthesis should have as high a portion of its original strength as possible for at least 3 days, and sometimes as much as 15 days or more, and preferably shold be completed absorbed by muscular tissue within from 45 to 90 days or more depending on the mass of the cross-section. The release time of drugs may vary over even wider time periods by choosing a matrix system where release rate gives a desired therapeutic effect.

In common with many biological systems, the requirements are not absolute and the rate of absorption as well as the short-term strength requirement varies from patient to patient and at different locations within the body, as well as with the thickness of the section of PGA.

The PGA may be formed as tubes or sheets for surgical repair and may also be spun as thin filaments and woven or felted to form absorbable sponges or absorbable gauze, or used in conjunction with other compressive structures as prosthetic devices within the body of a human or animal where it is desirable that the structure have short-term strength, but be absorbable. The useful embodiments include tubes, including branched tubes or Tees, for artery, vein or intestinal repair, nerve splicing, tendon splicing, sheets for tying up and supporting damaged kidney, liver or other internal organ, protecting damaged surface areas such as abrasions, particularly major abrasions, or areas where the skin and underlying tissues are damaged or surgically removed. Such elements may have incorporated therein a drug which is released to tissue over an appropriate period of time. Antibiotics are very useful in controlling pathogenic organisms. Many wounds are heavily contaminated. Steroids may be used to aid in expediting healing. The drug may be chosen for either local or systemic effect, depending upon the requirements of a therapeutic program.

The PGA may be exposed to moisture during storage before use, or may be of a lower molecular weight, both of which increase the rate of absorption by the body tissues, so that the surgical element has a faster rate of drug release.

The medical uses of PGA include, but are not necessarily limited to:

A. Pure PGA

1. Solid Products, molded or machined
   a. Orthopedic pins, clamps, screws and plates
   b. Clips (e.g., for vena cava)
   c. Staples
   d. Hooks, buttons and snaps
   e. Bone substitute (e.g., mandible prosthesis)
   f. Needles
   g. Non-permanent intrauterine devices (spermocide)
   h. Temporary draining or testing tubes or capillaries
   i. Surgical instruments
   j. Vascular implants or supports
   k. Vertebral discs
   l. Extracorporeal tubing for kidney and heart-lung machines
2. Fibrillar Products, knitted or woven, including velours
   a. Burn dressings
   b. Hernia patches
   c. Absorbent paper or swabs
   d. Medicated dressings
   e. Facial substitutes
   f. Gauze, fabric, sheet, felt or sponge for liver hemostasis
   g. Gauze bandages
   h. Dental packs
   i. Surgical sutures
3. Miscellaneous
   a. Flake or powder for burns or abrasions
   b. Foam as absorbable prosthesis
   c. Substitute for wire in fixations
   d. Film spray for prosthetic devices B. PGA in Combination with other Products 1. Solid Products, molded or machined
   a. Slowly digestible ion-exchange resin
   b. Slowly digestible drug release device (pill, pellet)
   c. Reinforced bone pins, needles, etc.
2. Fibrillar Products
   a. Arterial graft or substitutes
   b. Bandages for skin surfaces
   c. Burn dressings (in combination with other polymeric films.)

Any of these elements may have a drug incorporated for controlled release into tissue as a primary or secondary function.

One method of sterilizing PGA prostheses is by heat under such conditions that any microorganisms or deleterious materials are rendered inactive. Another is to sterilize using a gaseous sterilizing agent such as ehtylene oxide. Other methods of sterilizing include radiation by X-rays, gamma rays, neutrons, electrons, etc., or high intensity ultrasonic vibrational energy or combinations of these methods.

Different sterilizing procedures may be required which are compatible with the therapeutic agents present.

One of the early repositories meeting considerable acceptance was bees wax for penicillin. Penicillin was suspended in the bees wax, the mixture injected into a patient, and the penicillin thus released from the repository over a period of several days or longer. After the penicillin had been released, the bees wax remained in the subject as an undesired foreign body for an extended period of time.

PGA permits similar usage as a solid repository except that after the drug is released, te polymer itself dissolves or is digested or absorbed and leaves nothing as an undesired residue in the tissue.

Controlled release rates are very desirable. Some drugs are injected with the intention that the faster the drug is absorbed, the better. Others need to be emplaced under such conditions that the maximum concentration released is within desired limits, and yet the drug is made available over an extended period of time so that a single implantation can last for whatever length of time is desired for a particlar medical procedure. For instance, as a birth control pill, the blood levels of certain steroids arr to be maintained at a low level for prolonged periods. The steroid may be dissolved in chloroform, the present polymers added, the mixture dried and tabletted. By using PGA which is subjected to varying moisture exposure, the relative rate of release and absorption can be varied.

For contraceptive purposes, an effective storage bank may be desired with a prolonged release time. The medicament containing absorbable polymer may be shaped and used as an intrauterine contraceptive device, having the advantages of both shape and the released medicament, and additionally an inherently limited effective life. With other steroids used for the treatment of pathological conditions, the choice may be that the entire dosage is released uniformly over a period of from 1 to 30 days, or so. For other drugs the release period desired may be even more widely variable. For some antibiotics an effective concentration for 1 or 2 days is preferred for control of some pathogens.

The absorbable PGA may be ground and mixed with drugs and processed through a tabletting press, or the mixture may be moistened with a binding liquid and compressed. For instance, PGA may be mixed with steroids, and compressed either dry or with a binder, to a desired size and shape.

The PGA drug mixture may be used orally. PGA has a relatively slow hydrolysis rate in the acid environment in the stomach and a higher hydrolysis rate in the more alkaline environment of the intestine. For oral ingestion, any effective release must be achieved before the elimination of the residual PGA, which in humans is normally within 48 hours. The time in othe mammals may vary.

For implantation in tissues, either subcutaneously, intramuscularly, or in other areas, a glycolic acid polymer is used which gives the desired release rate and then after its therapeutic effect is achieved, the residual absorbable polymer is absorbed which clears the tissues of foreign bodies.

Whereas the repository as a sheet or pellet may be introduced beneath the skin, a convenient form is to shape the PGA medicament mixture as a thread, which is readily implantable beneath the skin as a suture, and which can be implanted at a cosmetically convenient location for systemic medicaments, or in selected area, for medicaments whose application is to be localized.

Additional materials such as silicones may be coated upon the polymer repository where it is desired that the release rate be further delayed. For instance, there are pathological conditions under which the release of a drug or hormone may be desired for the remaining life of a subject. In fact, the remaining life of a subject may be determined by an effective release of a drug from an implanted repository, or other source.

Sterility is essential in the subcutaneous implants, and desirable in oral forms. If the medicament is adaptable to radiation, heat, or ethylene oxide sterilizing cycles, such may be used. For more labile medicaments, the absorbable repository forms are made using sterile techniques from sterile components, or a sterilization procedure is chosen which is compatible with the medicament characteristics.

PGA can be considered as essentially a product of polymerization of glycolic acid, that is, hydroxyacetic acid.

Preferably, the molecular weight is in the range of about 10,000 or more. Above 500,000 the polymer is difficult to mold.

In these molecular weight ranges the polymer has a melt viscosity at 245°C. of between about 400 and about 27,000 poises. Because the PGA is from a synthetic and controllable source, with the controlled molecular weight and controlled small percentage of comonomer, the absorbability, stiffness, and other characteristics can be modified.

Among several methods by which PGA can be prepared, one preferred route involves the polymeriztion of glycolide,

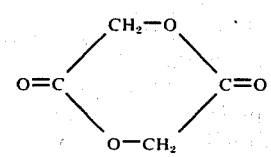

the cyclic dimeric condensation product formed by dehydrating hydroxyacetic acid. During polymerization of glycolide, the ring is broken and straight-chain polymerization occurs.

Small quantities of other materials may be present in the chain, as for example, d,l-lactic acid, its optically active forms, homologs, and analogs. In general, plasticizers tend to intefere with crystallinity, orientation, etc. and weaken the prosthesis but are useful for sponges and films.

Other substances may be present, such as dyes, antibiotics, antiseptics, antiseptics, anaesthetics, and antioxidants. Surfaces can be coated with a silicone, beeswax, and the like to modify handling or absorption rate.

Such antibiotics, antiseptics, or anaesthetics are released slowly, as the polyglycolic acid is absorbed by living tissue, and become available to exert their pharmacological action either at the site of the implant, or if absorbed and transported by the blood, elsewhere. Typical such components are furacin, tetracycline, chlortetracycline, oxytetracycline, sulfadiazine, lincomycin, sulfasymazine, etc.

The polymerization of glycolide occurs by heating with or without a catalyst, or may be induced by radiation such as X-rays, gamma rays, electron beams, etc. Polymers may also be obtained by condensing glycolic acid or chloracetic acid with or without a catalyst under a variety of conditions. Good moldable objects or fibers are most readily obtained when the melt viscosity at 245°C. is about 400 to about 27,000 poises.

Polyhydroxyacetic esters have been described in U.S. Pat. No. 2,668,162, Lowe, PREPARATION OF HIGH MOLECULAR WEIGHT POLYHYDROXYACETIC ESTER, and U.S. Pat. No. 2,676,945, Higgins, CONDENSATION POLYMERS OF HYDROXY- ACETIC ACID.

U.S. Pat. No. 2,668,162 — Lowe quantifies a small amount of lactides as up to 15%, disclosing, for example, that a preparation of a copolymer of 90/10 glycolide/lactide offers two advantages over the homopolymer of glycolide. One advantage is that the melting point of the copolymer is lower than the homopolymer, being in the nieghborhood of 200°C.; and the other that the entire reaction can be conducted at approximately the melting point of the copolymer. Operation at the lower temperatures decreases the rate of degradation of the polymer which gives a polymer of lighter color.

Example 4 of said U.S. Pat. No. 2,668,162 shows reaction conditions.

The processes described in the above two patents can be used for producing PGA from which repositories may be made.

Certain specific embodiments illustrative of this invention are set forth in the following examples, in which parts are by weight, unless otherwise clearly indicated:

EXAMPLE 1

100 Parts of recystallized glycolide (melting point 85.0° to 85.5°C.) are intimately mixed with 0.02 part of methoxyacetic acid, 0.03 part of phenoldisulfide (Santo-Nox), and 0.03 part antimony trifluoride. Separate glass tubes are each charged with approximately 20 grams of the mixture, deoxygenated by repeated evacuation and argon purging, then sealed under vacuum and heated to 185° to 190° C. for 4 1/2 hours. On cooling a white opaque tough PGA is produced in a 97.5% yield with a melt viscosity at 245° C. of 5,000 poises. The polymer is reheated and spun into filaments at a temperature of about 230° C. at a speed of about 150 feet per minute. The filaments produced are cooled, then drawn at about 55° C. When drawn to five times the original length a strong tough filament is produced. The dry filaments are in condition for use.

EXAMPLE 2

The polymer of the preceding example is formed into a plurality of smaller filaments, seven of which are twisted into a polyfilamentary strand, which is sterilized and used following the techniques of Example 1 .

Because it is a synthetic polymer, the methods of forming are more versatile than in starting with naturally occurring materials.

EXAMPLE 3

Into a suitable reaction vessel there is charged 400 parts of a commercial glycolic acid which is then heated from room temperature to about 200° C. over a period of about 4 hours. When the pot temperature has reached 185° C., the pressure of the system is reduced from atmospheric pressure to 15 mm. of Hg, causing the water of condensation and/or esterification to distill off. The residue is allowed to cool and is pulverized into about 280 parts of a powder which is then added in small increments to a suitable pyrolysis chamber maintained at a temperature of about 250–285° at a pressure of less than 15 mm. of Hg. The distillate, about 238 parts by weight, is dissolved in a minimum amount of hot ethyl acetate, and after decolorizing and purifying with active carbon, the distillate is recrystallized from the above solution to provide 160 parts of product having a melting point of about 82.5—84.0° C. The infrared spectrum confirms that the product is substantially pure glycolide.

The glycolide thus prepared is polymerized in the presence of an alcohol free of non-benzenoid unsaturation and free of any reactive groups other than alcoholic hydroxy groups and in the presence of $SnCl_2 \cdot 2H_2O$.

A heavy walled glass tube having a bore of about 3/10 inch and sealed at one end is charged with 3 parts of the substantially pure glycolide composition, 0.04 part of a 0.1% ether solution of $SnCl_2 \cdot 2H_2O$ (about 0.0013% of $SnCl_2 \cdot 2H_2O$ based on the weight of the substantially pure glycolide composition), 0.0166 part of lauryl alcohol (0.346 mole percent based on the moles of the substantially pure glycolide composition), and a magnetic steel ball 5/32 inch in diameter. The tube is evacuated and purged with argon. The tube is evacuated again to a vacuum of less than 1 mm. of Hg. and the top is sealed. The reaction tube is placed in a vertical position in a closed glass chamber throughout which dimethyl phthalate is refluxed at 222° C. The boiling point of the dimethyl phthalate is controlled by varying the pressure of the system. At periodic intervals after melting, the viscosity of the reaction mixture is measured by raising the steel ball by means of a magnet and measuring the rate of the fall of the ball in sec./in. Ninety minutes after the melt is first achieved, the ball drop time is 550 sec./in. or about 7200 poises, and after 120 minutes, the ball drop time is 580 sec./in. or about 7600 poises.

The PGA thus produced is spun into 0.002 inch diameter fibers and used to form strands.

The filaments are braided into strands which are the size of 00 sutures (about 0.013 inch), and dipped in a saturated aqueous solution of tetracycline hydrochloride. The strands are air dried, and are ready for use. If the thus impregnated sutures are to be stored for more than a few days, the sutures should be vacuum dried. A temperature of 80° C., at less than 1 mm. pressure for about an hour, and storage in a dry moisture proof container as set forth in U.S. Pat. No. 3,728,839, Glick, STORAGE STABLE SURGICALLY ABSORBABLE POLYGLYCOLIC ACID PRODUCTS, is effective. Dessicated storage gives long term stability. For use in a few days, the air dried suture gives excellent results. The suture shows full strength, and releases the tetracycline into the adjacent tissue. Usually, the wound clears itself of pathogens in a few days, and healing is noneventful. For contaminated traumatic wounds, the healing rate can vary widely depending on damage to adjacent tissue, and the type and quantity of pathogenic organisms introduced. Where there is poor vascularization, healing is slower.

The drug on the suture can be a steroid, or other medicament that aids in healing in a particular location or is to be systemically administered.

For longer release times, the medicament can be incorporated in the suture during spinning, if the medicament retains its efficacy under extrusion conditions.

The opaque PGA as synthesized in Example 1 can be ground with a therapeutic agent, or dissolved in a solvent, such as hexafluoroacetone sesquihydrate or hexafluoroisopropyl alcohol, in which the PGA is soluble and in which the medicament is soluble and non-reactive. The solution is cast into pellets and then dried. Care should be taken to remove all of the solvent before implantation of the pellets.

The repository containing the medicament, or controlled release medicament device may be shaped as a pellet for storage and release of the medicament only, or may be shaped as a clip or staple, or an intrauterine device. As a clip or staple, the repository may be shaped, as for example, a C-clamp to seve as a hemostat, or to retain tissue in position. As a hemostat, clamping action is required for a comparatively short period, a day or a few days usually, while the repository slowly releases its medicament charge to its host tissue.

As an intrauterine device, the repository can be shaped as a conventional insert IUD, for its mechanical action, and additionally a steroid is slowly released into an effective location, so that the steroid dosage requirements are minimal. The IUD dissolves and becomes inactive, so that removal is not necessary, and the user regains fertility. Reimplantation of an additional device provides longer term protection where desired.

The degree of polymerization and the hydrolytic effects of storage control the release rate, so that a desired release life can be incorporated into the repository.

Solid PGA has such tremendous strength that a surgical needle can be formed on the end of a PGA suture by either fusing the PGA of the suture, or molding additional PGA onto the suture end, the needle being bent and pointed as may be surgically preferred for a specific surgical procedure.

Becoming of increasing interest and importance is the implantation of cosmetic devices. For example, some women, due to partial surgical removal of breast tissue because of malignancies or traumatic injuries, are left with smaller breasts than are considered desirable.

A non-migrating prosthetic implantation has been used which consists of a plastic sponge or a plastic bag partially filld with a liquid having a viscosity adjusted to simulate that of natural tissue. The bag is implanted through a slit under the breast, to raise the mammary tissue away from the underlying chest wall which permits surgical reconstruction which has a very natural appearance and resilience. See U.S. Pat. No. 3,559,214 for surgical details.

It is found that if the implant to be used is constructed from a physiologically inert material such as polypropylene or a silicone film, the implant can be formed with a surface roughness in which, through loops, or fusion of filaments of polypropylene or other material there is formed an implant to which the non-absorbable filament are attached. If polyglycolic acid as a bi-component material is stitched, woven, felted or otherwise formed into such appendant structures, the element may be readily implaced and the polyglycolic acid portions are dissolved out with naturally occurring tissue replacing the polyglycolic acid and thus becoming intermeshed with the elements attached to the prosthetic implant which interlocks the bag in location in the body tissues, primarily the chest wall, and, hence, the implanted prosthetic device is firmly locked into the tissues and protected from accidental displacement.

In one embodiment, the implanted prosthetic device is an implantable bag containing viscous liquid therein, which may be a single cell or a sub-divided cell, with a puncturable area in a selected location so that after implantation, a hypodermic needle may be used to puncture through the skin and intervening tissues, the puncturable area and into the main volume of the prosthetic device which permits hypodermic removal or addition of additional liquid so that with a minimum inconvenience, time and expense, the enchancing volume may be modified with changing fashions or the desires of the user.

A similarly constructed element using the same co-joint bi-component displacing technique is available to fill out other areas in which external tissue contours are to be changed. For example, an individual may have been involved in an automobile accident or the victim of a tumor and with the removal of certain tissues, a disfiguring surface configuration remains. By filling it with a prosthetic element of suitable size and shape, the surface configuration can be reconstructed to the great psychological benefit of the subject.

Similar, but solid, devices may be implanted in the nose, chin or ears to modify, restore or correct the surface configuration of the subject. In some instances, it is found that the psychological benefit to the subject far overshadows any surgical risks, costs or inconveniences resulting from the operative technique.

A bi-component system can be used to aid in retaining implanted devices such as internal pacemakers or hearing aids. See U.S. Pat. No. 3,557,775, supra, for details of the surgical aspects.

We claim

1. A controlled release medicament device consisting of at least one filament of polyglycolic acid having incorporated therein a small but effective amount of an antibiotic.

2. A medicament repository consisting of a surgical element in the form of tubes, sheets, sponges, gauzes or prosthetic devices of polyglycolic acid having incorporated therein an effective amount of a medicament.

3. The repository of claim 2 which is functionally effective as a tissue retaining clip or staple, as well as having a medicament release function.

4. In a surgical needle and suture combination the improvement comprising:

a suture consisting of at least one filament of stretched and oriented normally solid polyglycolic acid, the said surgical needle and suture being sterile; the said suture having good knotability, good knot strength, good handleability, ready colorability, and a total denier of from 1 to 4,000, retaining a high proportion of its original strength for at least 3 days when embedded in living muscular tissue, being substantially absorbed in 90 days when embedded in living muscular tissue, and being substantially free from contaminants not absorbable by living muscular tissue, and having incorporated therein a small but effective quantity of an antibiotic, antiseptic, or anesthetic, 5. The suture of claim 4 having incorporated therein an antibiotic.

* * * * *